United States Patent
Guidot et al.

(10) Patent No.: US 7,291,750 B1
(45) Date of Patent: Nov. 6, 2007

(54) METHOD FOR DEHYDROGENOFLUORINATION OF AN AROMATIC CARBAMOYL FLUORIDE

(75) Inventors: Gilbert Guidot, Massanes (FR); Christophe Rochin, Princeton, NJ (US); Laurent Saint-Jalmes, Meyzieu (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 10/019,694

(22) PCT Filed: Jul. 4, 2000

(86) PCT No.: PCT/FR00/01912
§ 371 (c)(1),
(2), (4) Date: May 3, 2002

(87) PCT Pub. No.: WO01/02347
PCT Pub. Date: Jan. 11, 2001

(30) Foreign Application Priority Data
Jul. 5, 1999 (FR) .................................. 99 08647

(51) Int. Cl.
*C07C 263/00* (2006.01)

(52) U.S. Cl. .................................................. 560/348
(58) Field of Classification Search ............... 560/330, 560/336, 338, 348
See application file for complete search history.

(56) References Cited

U.S. PATENT DOCUMENTS 3,860,623 A * 1/1975 Zanker et al. .............. 560/348

FOREIGN PATENT DOCUMENTS

GB 955 898 A 4/1964

OTHER PUBLICATIONS

R. Appel et al., *Chemische Berichte*, vol. 107, (1974), pp. 2671-1674; XP002133040 Weinheim, DE.

* cited by examiner

*Primary Examiner*—Karl Puttlitz
(74) *Attorney, Agent, or Firm*—Buchanan, Ingersoll & Rooney, PC

(57) ABSTRACT

A method for dehydrogenofluorination for transforming an aromatic carbamoyl fluoride into a corresponding isocyanate, is provided. The method includes subjecting a carbamoyl fluoride to a temperature not less than 80° C. in a solvent wherein the carbamoyl fluoride is in a dissolved or finely dispersed state in the solvent. The method is applicable to organic synthesis.

48 Claims, No Drawings

METHOD FOR DEHYDROGENOFLUORINATION OF AN AROMATIC CARBAMOYL FLUORIDE

A subject matter of the present invention is a process which makes possible the treatment of an aromatic carbamoyl fluoride to result in the corresponding isocyanate.

A more particular subject matter of the present invention is a process of the preceding type which makes it possible to obtain a good degree of conversion, a good conversion yield, that is to say a good selectivity, and a good reaction yield.

Carbamoyl fluorides are rather uncommon compounds which have, however, experienced renewed interest because of the growing role of fluorinated derivatives in pharmacology and agrochemistry. This is because one of the most conventional techniques for synthesizing derivatives exhibiting a perfluorinated aliphatic carbon consists in blocking possible anilines in the form of an isocyanate, in chlorinating (generally the alkyl derivative position by means of radical chlorine, and then treating the chlorinated derivative obtained with a fluorinated medium, generally a medium comprising hydrofluoric acid in the liquid phase. During this type of process, the first reaction which takes place is the addition of hydro-fluoric acid to the isocyanate functional group to give a carbamoyl fluoride.

This carbamoyl fluoride is very difficult to convert into isocyanate. This is a great pity as the isocyanate is a very reactive intermediate which makes possible numerous syntheses and which in particular makes possible ready release of the corresponding aniline.

The first part of the reactions is disclosed in various documents and in particular in the document EP-A 152 310 and the document EP-A 129 214. As regards the conversion of the carbamoyl fluoride to the isocyanate, British patent No. 955 898, published on Apr. 22, 1964, on behalf of Bayer, indicates the possibility of carrying out this reaction, in particular in example 1. However, the technique used results in a low yield (35%), the reaction apparently being very difficult and resulting in particular in heavy products described as resins.

This is why one of the aims of the present invention is to provide a process which makes possible the conversion of carbamoyl fluoride to an isocyanate functional group under operating conditions which are easy to employ and which makes possible good reaction yields and good selectivity.

One of the main difficulties encountered during the study which led to the present invention is the very high reactivity of carbamoyl fluoride with respect to itself or with respect to rich aromatic rings.

These aims and others which will become apparent subsequently are achieved by means of a dehydrofluorination process which makes it possible to convert an aromatic carbamoyl fluoride to an isocyanate, in which process said carbamoyl fluoride is subjected to a temperature at least equal to 80° C., advantageously at least equal to 90° C., in a solvent and that, at said temperature of at least 80° C., said carbamoyl fluoride is in the dissolved or finely dispersed state in said solvent.

According to the present invention, it has thus been possible to demonstrate that the finely dispersed nature or the dissolved nature of the carbamoyl fluoride at a temperature where it is reactive plays a key role in the production of the isocyanate with a good yield.

The reaction will preferably be carried out at a temperature at most equal to 150° C.

Said solvent exhibits a boiling point (starting boiling point in the case of a mixture) advantageously of at least 100° C., more preferably of at least 120° C.

It is preferable to arrange for the pressure in the reactor to be such that the solvent is boiling (that is to say, in the great majority of cases, at reflux). A pressure greater than atmospheric pressure will thus be chosen if the solvent exhibits a boiling point lower than the temperature at which it is desired to operate and a pressure lower than atmospheric pressure will thus be chosen when the solvent has a boiling point higher than the temperature at which it is desired to operate.

According to one of the preferred implementations of the present invention, the solvent, which can moreover be a mixture of solvents, is chosen from those which are miscible with hydrofluoric acid.

This miscibility can be partial or complete but it is preferable for the miscibility to be such that the solvent, or the mixture of solvents, chosen exhibits an ability to dissolve the hydrofluoric acid which is at least equal to 5% by volume, preferably at least equal to 10% by volume. This solubility is of considerable advantage as this miscibility of the solvent with hydrofluoric acid makes it possible to use the latter as third solvent, facilitating the dissolution of the carbamoyl fluoride in the reaction mixture.

Consequently, according to a preferred form of the present invention, hydrofluoric acid is used to facilitate the introduction of the carbamoyl fluoride into the reaction mixture. This introduction can be carried out at low temperature or can be introduced at high temperature. During the heating or during the introduction, when the carbamoyl fluoride is introduced into a solvent heel, the hydrofluoric acid which helps in the dissolution is removed but, on being removed, it leaves the carbamoyl fluoride in a form which is either highly divided or even dissolved in the solvent used.

According to a preferred embodiment, during the introduction of the carbamoyl fluoride, the ratio of the hydrofluoric acid to the carbamoyl fluoride (HF to carbamoyl fluoride ratio) is at least equal to 2, advantageously to 3, preferably to 4.

According to one of the preferred implementations of the present invention, the addition of carbamoyl fluoride is carried out in the form of a solution of the latter in hydrofluoric acid, the ratios indicated above being observed.

The best results obtained correspond to the addition of a solution of carbamoyl fluoride to a solvent heel which is at the reaction temperature.

This solution is advantageously a solution in hydrofluoric acid, as indicated above.

In the case of an addition to a solvent heel, the addition must be carried out so as to control the ratio of the hydrofluoric acid present in the reaction medium, in this specific case including that added, more exactly in equilibrium with the carbamoyl fluoride, to the substrate.

In other words, the ratio of the hydrofluoric acid [the free hydrofluoric acid and that added to an isocyanate functional group (that is to say, in the form of carbamoyl fluoride)] and the isocyanate functional groups, real or masked in the carbamoyl fluoride form, is advantageously at most equal to 5, preferably at most equal to 0.3, more preferably at most equal to 0.1. This condition implies a relatively slow addition of the carbamoyl fluoride.

According to the present invention, it is particularly advantageous to avoid the presence of impurities having a chlorine in the benzyl position as, in the context of this reaction, these impurities appear to be highly reactive and would destroy a number of substrates or compounds deriving therefrom.

By way of indication, it is preferable for the number of molecules carrying chlorine in the benzyl functional group to be at most equal to 0.5 to 5%, advantageously to 2%, preferably to 1%, of the carbamoyl fluorides to be treated.

The substrates which are most suitable for the present invention are carbamoyl fluorides which comprise an aliphatic carbon with $sp^3$ hybridization carrying at least two fluorines. This aliphatic carbon is generally a benzyl carbon, that is to say that it is attached directly to an aromatic ring. However, it can be attached to the aromatic ring via a chalcogen (in particular oxygen).

The present invention is particularly suited to the case where said aromatic ring is that carrying the nitrogen of the carbamoyl functional group.

Such a substrate can comprise several of these aliphatic carbons carrying at least two fluorines.

Thus, the substrate advantageously corresponds to the formula:

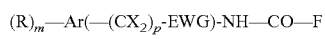

where:

Ar means an aromatic residue advantageously exhibiting at least one, preferably two, more particularly three, of the following characteristics:
  the residue is mononuclear, that is to say comprises only one ring;
  the residue is advantageously homocyclic;
  the residue has six ring members;
the X units, which are alike or different, represent a fluorine or a radical of formula $C_nF_{2n+1}$ with n an integer at most equal to 5, preferably to 2;
p represents an integer at most equal to 2;
a EWG represents a hydrocarbonaceous group or an electron-withdrawing group, the optional functional groups of which are inert under the reaction conditions, advantageously fluorine or a perfluorinated residue of formula $C_nF_{2n+1}$ with an integer at most equal to 8, advantageously to 5. The total carbon number of —$(CX_2)_p$-EWG is advantageously between 1 and 15, preferably between 1 and 10.
m is 0 or an integer chosen within the closed range (that is to say, comprising the limits) 1 to 4;
R is a substituent which is inert under the operating conditions and which is advantageously chosen from halogens, advantageously light halogens (that is to say, chlorine and fluorine), and hydrocarbonaceous radicals, preferably alkyl, aryl, alkylchalcogenyl (such as alkyloxy) or arylchalcogenyl (such as aryloxy) radicals.

The substrate compound can in particular have the formula (the optional substituents inert under the reaction conditions are not displayed):

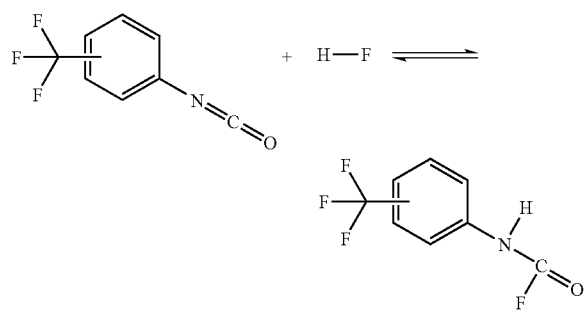

Advantageously, R is an aryl or alkyl hydrocarbonaceous radical, advantageously with at most 10 carbon atoms, preferably with at most 5 carbon atoms, R can also be carboxyl functional groups, nitrites, ketones and fluorocarbonyls.

The preferred substituents are either nothing, that is to say hydrogen, or aryls or alkyls or alkyloxys.

R or at least one of the R groups can also be a group comprising a carbon carrying at least two fluorines, of formula $CX_{2p}$-EWG as above.

The following examples illustrate the invention.

EXAMPLE 1

Elimination of Hydrofluoric Acid in a Solvent Capable Of Dissolving the Carbamoyl Fluoride The solid carbamoyl fluoride (0.1 mol) is charged to a 180 ml Teflon reactor capable of with-standing hydrofluoric acid which is heated by a regulated oil bath and is magnetically stirred. Tri-chlorobenzene (chlorinated in the 1, 3 and 4 position) is then charged in an amount of 100.4 g.

This results in a suspension easily to be heated. The medium is gradually heated to 80° C. and becomes homogeneous, translucent and orange yellow. Evolution of gas begins in the vicinity of 100° C. and becomes significant from 105° C. The temperature is raised to 125° C. and heated for 7 hours. After cooling, a mass corresponding to an isolated yield of 80% is recovered.

The compound is subsequently subjected to distillation and a yield of 73% in solution in tri-chlorobenzene is recovered, some resins remaining in the distillation residue.

EXAMPLE 2

Different tests were carried out using mono-chlorobenzene as solvent according to various procedures. The most commonly employed procedure is as follows:

A) Preparation of the Carbamoyl Fluoride Solution
  HF is introduced into a reactor at a temperature of −5° C. The trichloromethylphenyl isocyanate which it is desired to convert is then introduced at the desired fluorination temperature, the fluorination lasts 1 h 30, unless indicated otherwise in the subsequent table, and a finishing operation is carried out for 4 h at the temperature indicated in the table. It will be observed that, when everything is otherwise the same apart from the finishing temperature, the yields are better when the finishing temperature is brought to a relatively high temperature, that is to say approximately 20-25° C. This phenomenon shows the extremely harmful effect of small amounts of derivatives remaining chlorinated just the once in the benzyl position.

B) Reversion to isocyanate
  The carbamoyl fluoride solution, which may or may not have been subjected to removal of HF beforehand, is introduced into a reactor under the conditions specified in the table below. The heating, pressure and temperature conditions are also specified in the table.

The results are collated in the following table:

| No. of the test | HF 07 | HF 08 | HF 09 | HF 10 | HF 11 | HF 12 | HF 13 | HF 14 | HF 15 | HF 16 |
|---|---|---|---|---|---|---|---|---|---|---|
| Fluorination temperature | −5° C. | −5° C. | −5° C. | 2° C. | 2° C. | 2° C. | 2° C. | −5° C. | −5° C. | −5° C. |
| Finishing temperature | 2° C. | 2° C. | 20° C. | 20° C. | 20° C. | 20° C. | 20° C. | 20° C. | 25° C. | 25° C. |
| HF removal beforehand | No | Yes | No | Yes | No | No | No | No | Yes | Yes |
| HF released during the distillation-reaction | 10 | 10 | 10 | 4.99 | 4.93 | 5.72 | 9.87 | 8.93 | 3.72 | 3.34 |
| Pressure | Atmospheric | Atmospheric | Atmospheric | Vacuum (300 mm) | Vacuum (300 mm) | Atmospheric | Atmospheric | Atmospheric | 2 atm | 2 atm |
| Batch or Semi-continuous | Semi-cont. | Batch | Semi-cont. | Batch | Semi-cont. | Semi-cont. | Semi-cont. | Semi-cont. | Semi-cont. | Semi-cont. |
| Running onto MCB (duration) | 1 h 45 | | 0 4 h | | 0 2 h | 4 h | 4 h | 4 h | 4 h | 4 h |
| Temp, starting-final | 130-130° C. (reflux) | 20-130° C. (reflux) | 130-130° C. (reflux) | 48-100° C. (reflux) | 100-100° C. (reflux) | 130-130° C. (reflux) | 130-130° C. (reflux) | 130-130° C. (reflux) | 140-150° C. (reflux) | 130-130° C. (reflux) |
| Duration of the rise | None | 3 h | None | 1 h | None | None | None | None | None | None |
| Duration of the maintenance | 2 h 30 | 3 h | 2 h | | 0 | 0 2 h | 2 h | 2 h | 2 h | 2 h |
| Mole, starting | 1.67 | 1.67 | 1.67 | 1.66 | 1.66 | 1.63 | 1.67 | 1.86 | 1.86 | 1.67 |
| Mole before distillation | 1.18 | 1.35 | 1.51 | 1.42 | 1.35 | 1.35 | 1.55 | 1.46 | 1.43 | 1.36 |
| $COF_2$ evolution | 0.05 | 0.05 | 0.05 | 0.09 | 0.09 | 0.08 | 0.06 | 0.7 | 0.11 | 0.1 |
| Yd | 70.66% | 80.84% | 90.42% | 85.54% | 81.33% | 82.82% | 92.81% | 78.49% | 76.88% | 81.44% |
| Distillation Yd | 99.00% | 84.00% | 93.00% | 100.00% | 85.00% | 97.00% | 90.00% | 100.00% | 104.00% | 95.00% |
| Total Yd after distillation | 70.00% | 68.00% | 84.00% | 85.00% | 76.00% | 80.00% | 83.00% | 79.00% | 80.00% | 78.00% |
| Distribution of the light compounds in the final reaction mixture before distillation | | | | | | | | | | |
| Carbamoyl fluoride | | | 0.70% | 3.00% | 1.43% | 0.47% | 0.34% | 2.30% | 1% | 4.50% |
| Dimer | | | 0.90% | 2.50% | 1.60% | 1.10% | 0.98% | 0.80% | 1% | 0.90% |
| Urea | | | 1.10% | 2.00% | 1.00% | 2.50% | 1.60% | 1.00% | 1% | 1.30% |
| Biuret | | | 6.60% | 12% | 12.40% | 10.00% | 7.10% | 10.50% | 16% | 15.10% |
| Isocyanate | 82.93% | 77.59% | 90.70% | 80.50% | 83.57% | 85.93% | 89.98% | 85.40% | 81% | 78.20% |
| Isocyanate/biuret ratio | | | 13.74242424 | 6.708333333 | 6.739516129 | 8.593 | 12.67323944 | 8.133333333 | 5.0625 | 5.178807947 |

Comment on the Above Results

Tests HF 07 and HF 08, although not really bad, give a relatively mediocre yield of final isocyanate. The explanation of this phenomenon is related to the low finishing temperature, which leaves a not insignificant proportion of greater than 2 or 3% of monochlorodifluoromethylphenyl.

Another reason why test HF 07 is mediocre is the speed with which the carbamoyl fluoride solution is run in, which operation lasts only 1 h 45, whereas, in the other cases, it lasts significantly longer.

For tests HF 07 and HF 08, data on the impurities are lacking and consequently not very much can be concluded therefrom. For the tests for which this data is present, the isocyanate/biuret ratio can be used as an index of the selectivity of the reaction.

The reaction HF 09 gives very good results, both with regard to the overall yield and with regard to the purity of the product obtained. This demonstrates the advantage, first, of adding the carbamoyl fluoride in a form dissolved in hydrofluoric acid and, secondly, of operating with a high HF/carbamoyl fluoride ratio. In that case, the HF/isocyanate ratio is 10, which corresponds to the hydro-fluoric acid/carbamoyl fluoride ratio of 9. The results of tests HF 10 and HF 11 under vacuum are certainly good but slightly disappointing in view of the fact of having operated under vacuum. However, the rate of addition or the rate of temperature rise was doubtless a little too high.

Test HF 12 is very similar to test HF 09 but the difference with the latter results from the lower content of hydrofluoric acid in the mixture, more exactly the solution added.

In test HF 13, high levels of hydrofluoric acid are again found and thus a much better selectivity of the reaction.

Tests HF 15 and HF 16 show the effect of the increase in the pressure, which is not very favorable.

The invention claimed is:

1. A dehydrofluorination process to convert an aromatic carbamoyl fluoride to the corresponding isocyanate, the process comprising dehydrofluorinating the aromatic carbamoyl fluoride by gradually introducing the aromatic carbamoyl fluoride in a dissolved or finely dispersed state in a solvent into a solvent heel at a temperature of at least 80° C. to obtain the corresponding isocyanate, where the solvent heel comprises hydrofluoric acid and where the introduction controls the ratio of hydrofluoric acid, including free hydrofluoric acid and hydrofluoric acid added to isocyanate groups, to isocyanate functional groups, real or masked in carbamoyl fluoride form.

2. The process as claimed in claim 1, wherein the temperature of the solvent heel is at most equal to 150° C.

3. The process as claimed in claim 1, wherein said solvent exhibits a boiling point of at least 100° C.

4. The process as claimed in claim 1, wherein the reaction is carried out at a pressure such that, at the reaction temperature, the solvent is boiling.

5. The process as claimed in claim 1, wherein the solvent is miscible with hydrofluoric acid and does not react with the carbamoyl fluoride.

6. The process as claimed in claim 1, wherein said carbamoyl fluoride is introduced into the solvent with hydrofluoric acid.

7. The process as claimed in claim 1, wherein the addition of the carbamoyl fluoride to the solvent is carried out at a rate such that, in the ten final 90% of the reaction duration taking place below 100° C., the molar ratio of hydrofluoric acid to isocyanate (HF acid/aromatic isocyanate) is always less than 0.5.

8. The process as claimed in claim 1, wherein the carbamoyl fluoride substrate comprises an aliphatic carbon, that is sp³ hybridized, bearing at least two fluorines.

9. The process as claimed in claim 8, wherein said aliphatic carbon bearing at least two fluorines is a benzyl carbon and is directly attached to an aromatic ring.

10. The process as claimed in claim 9, wherein said aromatic ring is that bearing the nitrogen of the carbamoyl functional group.

11. The process as claimed in claim 1, wherein the reaction mixture comprises less than 1%, with respect to the starting carbamoyl fluoride, expressed as moles, of impurities exhibiting a chlorine in the benzyl position.

12. The process as claimed in claim 1, wherein the carbamoyl fluoride corresponds to the formula:

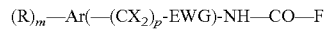

where:
Ar is an aromatic residue;
the X units, which are alike or different, represent a fluorine or a radical of formula $C_nF_{2n+1}$ with n an integer at most equal to 5;
p represents an integer at most equal to 2;
EWG represents a hydrocarbonaceous group or an electron-withdrawing group, the optional functional groups of which are inert under the reaction conditions;
the total carbon number of $-(CX_2)_p$-EWG is between 1 and 15;
m is 0 or an integer from 1 to 4;
R represents alike or different radicals comprising halogens or hydrocarbonaceous radicals.

13. The process as claimed in claim 1, wherein the solvent is a chlorobenzene.

14. The process as claimed in claim 13, wherein the chlorobenzene is a monochlorobenzene, a dichlorobenzene or a trichlorobenzene.

15. A dehydrofluorination process to convert an aromatic carbamoyl fluoride to the corresponding isocyanate, the process comprising dehydrofluorinating the aromatic carbamoyl fluoride by subjecting the aromatic carbamoyl fluoride to a temperature at least equal to 80° C. by gradually introducing the aromatic carbamoyl fluoride in a dissolved or finely disposed state in a solvent at a temperature of at least 80° C. to obtain the corresponding isocyanate, wherein the carbamoyl fluoride is introduced into the solvent with hydrofluoric acid in the form of a solution comprising anhydrous hydrofluoric acid, wherein the introduction controls the ratio of hydrofluoric acid, including free hydrofluoric acid and hydrofluoric acid added to isocyanate groups, to isocyanate functional groups, real or masked in carbamoyl fluoride form.

16. A dehydrofluorination process to convert an aromatic carbamoyl fluoride to the corresponding isocyanate, the process comprising dehydrofluorinating the aromatic carbamoyl fluoride by subjecting the aromatic carbamoyl fluoride to a temperature at least equal to 80° C. by gradually introducing the aromatic carbamoyl fluoride in a dissolved or finely disposed state in a solvent at a temperature of at least 80° C., wherein the introduction controls the ratio of hydrofluoric acid, including free hydrofluoric acid and hydrofluoric acid added to isocyanate groups, to isocyanate functional groups, real or masked in carbamoyl fluoride form, to obtain the corresponding isocyanate so that the total yield of the corresponding isocyanate is at least about 70%.

17. A dehydrofluorination process to convert an aromatic carbamoyl fluoride to the corresponding isocyanate, the process comprising dehydrofluorinating the aromatic carbamoyl fluoride by gradually introducing the aromatic carbamoyl fluoride in a dissolved or finely dispersed state with hydrofluoric acid in a solvent into a solvent heel at a temperature of at least 80° C. to obtain the corresponding isocyanate, wherein during introduction of the carbamoyl fluoride, the ratio of hydrofluoric acid to carbamoyl fluoride is at least equal to 2.

18. The process of claim 17, wherein the ratio of hydrofluoric acid to carbamoyl fluoride is at least equal to 3.

19. The process of claim 17, wherein the ratio of hydrofluoric acid to carbamoyl fluoride is at least equal to 4.

20. A dehydrofluorination process to convert an aromatic carbamoyl fluoride to the corresponding isocyanate, the process comprising dehydrofluorinating the aromatic carbamoyl fluoride by gradually introducing the aromatic carbamoyl fluoride in a dissolved or finely dispersed state with hydrofluoric acid in a solvent into a solvent heel at a temperature of at least 80° C., to obtain the corresponding isocyanate, wherein the ratio of hydrofluoric acid, including free hydrofluoric acid and added hydrofluoric acid, to isocyanate groups, real or masked in carbamoyl fluoride form, is at most equal to 0.5.

21. The process of claim 20, wherein the ratio of hydrofluoric acid to isocyanate groups is at most equal to 0.3.

22. The process of claim 20, wherein the ratio of hydrofluoric acid to isocyanate groups is at most equal to 0.1.

23. The process as claimed in claim 17, wherein the temperature of the solvent heel is at most equal to 150° C.

24. The process as claimed in claim 17, wherein said solvent exhibits a boiling point of at least 100° C.

25. The process as claimed in claim 17, wherein the reaction is carried out at a pressure such that, at the reaction temperature, the solvent is boiling.

26. The process as claimed in claim 17, wherein the solvent is miscible with hydrofluoric acid and does not react with the carbamoyl fluoride.

27. The process as claimed in claim 17, wherein said carbamoyl fluoride is introduced into the solvent with hydrofluoric acid.

28. The process as claimed in claim 17, wherein the addition of the carbamoyl fluoride to the solvent is carried out at a rate such that, in the final 10% of the reaction duration taking place below 100° C., the molar ratio of hydrofluoric acid to isocyanate (HF acid/aromatic isocyanate) is always less than 0.5.

29. The process as claimed in claim 17, wherein the carbamoyl fluoride substrate comprises an aliphatic carbon, that is $sp^3$ hybridized, bearing at least two fluorines.

30. The process as claimed in claim 29, wherein said aliphatic carbon bearing at least two fluorines is a benzyl carbon and is directly attached to an aromatic ring.

31. The process as claimed in claim 30, wherein said aromatic ring is that bearing the nitrogen of the carbamoyl functional group.

32. The process as claimed in claim 17, wherein the reaction mixture comprises less than 1%, with respect to the starting carbamoyl fluoride, expressed as moles, of impurities exhibiting a chlorine in the benzyl position.

33. The process as claimed in claim 17, wherein the carbamoyl fluoride corresponds to the formula:

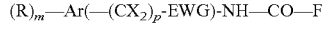

$(R)_m$—Ar(—$(CX_2)_p$-EWG)-NH—CO—F where:
Ar is an aromatic residue;
the X units, which are alike or different, represent a fluorine or a radical of formula $C_nF_{2n+1}$, with n an integer at most equal to 5;
p represents an integer at most equal to 2;
EWG represents a hydrocarbonaceous group or an electron-withdrawing group, the optional functional groups of which are inert under the reaction conditions;
the total carbon number of —$(CX_2)_p$-EWG is between 1 and 15;
m is 0 or an integer from 1 to 4;
R represents alike or different radicals comprising halogens or hydrocarbonaceous radicals.

34. The process as claimed in claim 17, wherein the solvent is a chlorobenzene.

35. The process as claimed in claim 34, wherein the chlorobenzene is a monochlorobenzene, a dichlorobenzene or a trichlorobenzene.

36. The process as claimed in claim 20, wherein the temperature of the solvent heel is at most equal to 150° C.

37. The process as claimed in claim 20, wherein said solvent exhibits a boiling point of at least 100° C.

38. The process as claimed in claim 20, wherein the reaction is carried out at a pressure such that, at the reaction temperature, the solvent is boiling.

39. The process as claimed in claim 20, wherein the solvent is miscible with hydrofluoric acid and does not react with the carbamoyl fluoride.

40. The process as claimed in claim 20, wherein said carbamoyl fluoride is introduced into the solvent with hydrofluoric acid.

41. The process as claimed in claim 20, wherein the addition of the carbamoyl fluoride to the solvent is carried out at a rate such that, in the ten final 90% of the reaction duration taking place below 100° C., the molar ratio of hydrofluoric acid to isocyanate (HF acid/aromatic isocyanate) is always less than 0.5.

42. The process as claimed in claim 20, wherein the carbamoyl fluoride substrate comprises an aliphatic carbon, that is $sp^3$ hybridized, bearing at least two fluorines.

43. The process as claimed in claim 42, wherein said aliphatic carbon bearing at least two fluorines is a benzyl carbon and is directly attached to an aromatic ring.

44. The process as claimed in claim 43, wherein said aromatic ring is that bearing the nitrogen of the carbamoyl functional group.

45. The process as claimed in claim 20, wherein the reaction mixture comprises less than 1%, with respect to the starting carbamoyl fluoride, expressed as moles, of impurities exhibiting a chlorine in the benzyl position.

46. The process as claimed in claim 20, wherein the carbamoyl fluoride corresponds to the formula:

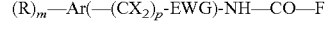

$(R)_m$—Ar(—$(CX_2)_p$-EWG)-NH—CO—F where:
Ar is an aromatic residue;
the X units, which are alike or different, represent a fluorine or a radical of formula $C_nF_2n+_1$ with n an integer at most equal to 5;
p represents an integer at most equal to 2;
EWG represents a hydrocarbonaceous group or an electron-withdrawing group, the optional functional groups of which are inert under the reaction conditions;

the total carbon number of —$(CX_2)_p$-EWG is between 1 and 15;

m is 0 or an integer from 1 to 4;

R represents alike or different radicals comprising halogens or hydrocarbonaceous radicals.

47. The process as claimed in claim 20, wherein the solvent is a chlorobenzene.

48. The process as claimed in claim 47, wherein the chlorobenzene is a monochlorobenzene, a dichlorobenzene or a trichlorobenzene.

* * * * *